United States Patent
Gruenbacher et al.

(10) Patent No.: US 9,439,993 B2
(45) Date of Patent: *Sep. 13, 2016

(54) APPARATUS FOR DELIVERING A VOLATILE MATERIAL

(71) Applicant: The Procter & Gamble Company, Cincinnati, OH (US)

(72) Inventors: Dana Paul Gruenbacher, Fairfield, OH (US); Jason John Olchovy, West Chester, OH (US); Scott Kendyl Stanley, West Chester, OH (US); James Douglas Still, Cleves, OH (US); Walter Sordo, Trento (IT); Stefano Deflorian, Trento (IT); Cedric Morhain, Cerdanyola del Valles (ES)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/217,955

(22) Filed: Mar. 18, 2014

(65) Prior Publication Data

US 2014/0197246 A1     Jul. 17, 2014

Related U.S. Application Data

(63) Continuation of application No. 12/694,637, filed on Jan. 27, 2010, now Pat. No. 8,740,110.

(60) Provisional application No. 61/169,840, filed on Apr. 16, 2009.

(30) Foreign Application Priority Data

Apr. 16, 2009 (CA) ..................................... 2662806

(51) Int. Cl.
*A61L 9/04* (2006.01)
*A61L 9/12* (2006.01)

(52) U.S. Cl.
CPC .................. *A61L 9/12* (2013.01); *A61L 9/127* (2013.01); *A61L 2209/131* (2013.01)

(58) Field of Classification Search
CPC .................... A61L 2209/133; A61L 2209/13; A61L 9/015; A61L 9/03; A61L 9/04; A61L 9/12; A61L 9/127; A61L 2209/131
USPC ................ 239/34-60; 222/83, 83.5, 85, 86; 220/501, 503, 521; 206/222, 532
See application file for complete search history.

(56) References Cited

U.S. PATENT DOCUMENTS 3,169,665 A    2/1965  Colley
3,351,495 A    11/1967 Larsen et al.
(Continued)

FOREIGN PATENT DOCUMENTS

EP    1 118 338 A2    7/2001
EP    1118338 A2      7/2001
(Continued)

OTHER PUBLICATIONS

All Office Actions, U.S. Appl. No. 15/005,224.
(Continued)

*Primary Examiner* — Jason Boeckmann
(74) *Attorney, Agent, or Firm* — Abbey A. Lopez; Amy I. Ahn-Roll (57) ABSTRACT

An apparatus for delivering a volatile material in a continuous manner is disclosed. The apparatus includes a delivery engine having a reservoir for containing a volatile material; a rupturable substrate secured to the reservoir; a rupture element positioned adjacent to the rupturable substrate; and a breathable membrane enclosing the reservoir, rupturable substrate and rupture element. In some embodiments, the apparatus includes a housing having a notch for compressing the rupture element and breaching the rupturable substrate as it is inserted into the housing.

14 Claims, 7 Drawing Sheets

(56) References Cited

U.S. PATENT DOCUMENTS

| | | | |
|---|---|---|---|
| 3,727,840 | A | 4/1973 | Nigro |
| 4,161,283 | A | 7/1979 | Hyman |
| 4,161,284 | A | 7/1979 | Rattan |
| 4,339,079 | A | 7/1982 | Sato et al. |
| 4,387,849 | A | 6/1983 | Van Loveren et al. |
| 4,526,320 | A | 7/1985 | Von Philipp |
| 4,630,775 | A | 12/1986 | Mandon |
| 4,762,275 | A | 8/1988 | Herbert et al. |
| 4,824,707 | A | 4/1989 | Spector |
| 4,947,578 | A | 8/1990 | Anderson |
| 4,995,555 | A | 2/1991 | Woodruff |
| 5,000,383 | A | 3/1991 | Van der Heijden |
| 5,230,867 | A | 7/1993 | Kunze et al. |
| 5,253,008 | A | 10/1993 | Konishi et al. |
| 5,455,043 | A | 10/1995 | Frischel-Ghodsian |
| 5,749,520 | A | 5/1998 | Martin |
| 5,875,968 | A | 3/1999 | Miller et al. |
| 6,553,712 | B1 | 4/2003 | Majerowski |
| 6,583,106 | B2 | 6/2003 | Zofchak |
| 7,481,380 | B2 | 1/2009 | Kvietok et al. |
| 7,498,369 | B2 | 3/2009 | Whear et al. |
| 7,754,938 | B2 | 7/2010 | Rashid |
| 7,883,028 | B2 | 2/2011 | McGee et al. |
| 8,696,982 | B2 * | 4/2014 | Gruenbacher et al. ........... 422/5 |
| 8,709,337 | B2 * | 4/2014 | Gruenbacher et al. ........... 422/5 |
| 8,740,110 | B2 * | 6/2014 | Gruenbacher ......... A61L 9/127 220/501 |
| 8,931,711 | B2 * | 1/2015 | Gruenbacher et al. ......... 239/34 |
| 2003/0089791 | A1 | 5/2003 | Chen |
| 2003/0190255 | A1 | 10/2003 | Boden |
| 2004/0003724 | A1 | 1/2004 | Ellis |
| 2005/0095264 | A1 | 5/2005 | Tollens et al. |
| 2005/0127538 | A1 | 6/2005 | Fabrega et al. |
| 2005/0211790 | A1 | 9/2005 | Kvietok et al. |
| 2005/0247802 | A1 | 11/2005 | Varanasi |
| 2006/0076429 | A1 | 4/2006 | Kvietok et al. |
| 2006/0097065 | A1 | 5/2006 | Kvietok et al. |
| 2006/0097066 | A1 | 5/2006 | Kvietok et al. |
| 2006/0121269 | A1 | 6/2006 | Miller et al. |
| 2006/0175425 | A1 * | 8/2006 | McGee et al. ................. 239/44 |
| 2006/0231641 | A1 | 10/2006 | Uchiyama et al. |
| 2006/0233538 | A1 | 10/2006 | Tollens et al. |
| 2006/0237555 | A1 | 10/2006 | Cetti et al. |
| 2007/0237498 | A1 | 10/2007 | Helf et al. |
| 2008/0191050 | A1 | 8/2008 | Blondeau et al. |
| 2009/0188986 | A1 | 7/2009 | Blondeau et al. |
| 2010/0154822 | A1 | 6/2010 | Reed et al. |
| 2010/0264232 | A1 | 10/2010 | Gruenbacher et al. |
| 2010/0308130 | A1 | 12/2010 | Gruenbacher |
| 2010/0314461 | A1 | 12/2010 | Gruenbacher et al. |
| 2011/0180621 | A1 | 7/2011 | Gruenbacher |

FOREIGN PATENT DOCUMENTS

| | | |
|---|---|---|
| FR | 1231135 | 9/1960 |
| JP | 61051833 | 3/1986 |
| JP | 61051834 | 3/1986 |
| JP | 63184040 | 7/1988 |
| JP | 03070139 | 3/1991 |
| JP | 05029540 | 2/1993 |
| JP | A-H5-345832 | 12/1993 |
| JP | 07037188 | 2/1995 |
| JP | 10085313 | 4/1998 |
| JP | 2005-029540 | 2/2005 |
| JP | 2005-261805 | 9/2005 |
| JP | A-2005-239772 | 9/2005 |
| JP | 2006-247479 | 9/2006 |
| JP | A-2008-056613 | 3/2008 |
| JP | 2008-087816 | 4/2008 |
| WO | WO 88/08721 | 11/1988 |
| WO | WO 9712518 A1 | 4/1997 |
| WO | WO 98/16262 | 4/1998 |
| WO | WO 98/16262 A1 | 4/1998 |
| WO | WO 2006/007559 A2 | 1/2006 |
| WO | WO 2006/029252 A1 | 3/2006 |
| WO | WO 2008/038706 | 3/2008 |
| WO | WO 2009/024802 A1 | 2/2009 |
| WO | WO 2009/024802 A1 | 6/2009 |

OTHER PUBLICATIONS

All Office Actions, U.S. Appl. No. 12/760,848.

* cited by examiner

Fig. 11

APPARATUS FOR DELIVERING A VOLATILE MATERIAL

FIELD OF THE INVENTION

The present invention relates to an apparatus having a breathable membrane for delivering a volatile material to the atmosphere in a continuous manner.

BACKGROUND OF THE INVENTION

It is generally known to use a device to evaporate a volatile material into a space, particularly a domestic space, in order to deliver a variety of benefits, such as air freshening or perfuming of the air. Non-energized systems, for example, systems that are not powered by electrical energy, are a popular way for the delivery of volatile materials into the atmosphere. These systems can be classified into those that require human actuation, such as aerosols, and those which do not required human actuation, such as wick based systems and gels. The first type delivers the volatile materials on demand and the second type in a more continuous manner.

One type of apparatus for delivering a volatile material is disclosed in U.S. Pat. No. 4,161,283. It discloses an article for delivering a volatile material comprising a reservoir, polymeric sheet or membrane, and a barrier layer releasably bonded to the outer wall of the reservoir. One drawback with this type of article is its susceptibility to de-lamination and leakage because the volatile materials are in contact with the membrane during storage or non-use. Another drawback may be that volatile materials build up in the membrane during storage, resulting in a spike in intensity immediately after the barrier layer is removed. Another drawback may be that the peel force makes it is difficult to remove the barrier layer without damaging the polymeric sheet or membrane. Yet another drawback may be the selectivity of the membrane in that it does not easily allow low vapor pressure volatile materials to diffuse through the polymer.

Another apparatus for delivering a volatile material is disclosed in U.S. Pat. No. 4,824,707. It discloses a decorative air freshener unit having a capsule containing a supply of volatile fragrance. The capsule is trapped between a microporous sheet and a backing sheet. The capsule is ruptured by applied force and the released fragrance is absorbed into the microporous sheet which gradually exudes the fragrance. This approach may limit the longevity of a scent since liquid is released all at once to the microporous sheet, and there is little control over the manner in which the liquid will wet the microporous sheet.

As such, there exists a need for an apparatus for delivering, over a period of time, a consistent release of volatile materials having a broad range of molecular weights and vapor pressures.

SUMMARY OF THE INVENTION

According to one embodiment of the invention, there is provided an apparatus for delivering a volatile material comprising a delivery engine having a reservoir for containing a volatile material; a rupturable substrate secured to the reservoir; a rupture element positioned adjacent to the rupturable substrate; and a microporous membrane enclosing the reservoir, rupturable substrate, and rupture element. The apparatus may deliver a volatile material in a continuous manner. In one aspect of the invention, the apparatus comprises a housing for the delivery engine. The housing may have vents for facilitating the diffusion of volatile materials from the delivery engine.

According to another embodiment of the invention, there is provided an apparatus for delivering a volatile material comprising a delivery engine having a liquid reservoir for containing a volatile material; a rupturable substrate secured to the reservoir; a compressible flange positioned adjacent to the rupturable substrate for rupturing the rupturable substrate; a collection basin in fluid communication with the liquid reservoir upon rupturing the rupturable substrate; and a breathable membrane enclosing the liquid reservoir, rupturable substrate, rupture element, and collection basin.

According to yet another embodiment of the invention, there is provided an apparatus for delivering a volatile material comprising a delivery engine having a liquid reservoir for containing a volatile material comprising a single opening; a rupturable substrate enclosing the single opening; a rupture element; a collection basin in fluid communication with the liquid reservoir upon rupturing the rupturable substrate; and a breathable membrane enclosing the liquid reservoir, rupturable substrate, rupture element, and collection basin. The breathable membrane has an evaporative surface area of about 15 $cm^2$ to about 35 $cm^2$ and has an average pore size of about 0.02 microns. The apparatus also comprises a housing for receiving and releasably engaging the delivery system. The housing has a rib for guiding the delivery engine and a notch for compressing the rupture element upon insertion of the delivery engine into the housing.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

FIG. 1 shows a perspective view of one embodiment of an apparatus in accordance with the present invention.

FIG. 2 shows an exploded, perspective view of one embodiment of a delivery engine in accordance with the present invention.

FIG. 3 shows a cross-sectional view of another embodiment of a rupture element in accordance with the present invention.

FIG. 4 shows a cross-sectional view of another embodiment of a rupture element in accordance with the present invention.

FIG. 5 shows a side elevational view of the delivery engine in FIG. 2 in accordance with the present invention.

FIG. 6 shows a front elevational view of one embodiment of a housing in accordance with the present invention.

FIG. 7 shows a top plan view of the housing in FIG. 6.

FIG. 8 shows a cross-sectional view along lines 8-8 of the apparatus in FIG. 1.

FIG. 9 shows the cross-sectional view in FIG. 8 where the delivery engine is being received by the housing.

FIG. 10 is a graph showing evaporation profiles of volatile materials having varying vapor pressure ranges evaporated from a breathable membrane in accordance with the present invention FIG. 11 is a graph showing evaporation profiles of volatile materials evaporated from a polyethylene membrane and from a breathable membrane in accordance with the present invention.

DETAILED DESCRIPTION OF THE INVENTION

The present invention relates to a non-energized apparatus for the delivery of a volatile material to the atmosphere in a continuous, non-energized manner. "Non-energized" means that the apparatus is passive does not require to be powered by a source of external energy. In particular, the apparatus does not need to be powered by a source of heat, gas, or electrical current, and the volatile material is not delivered by aerosol means. Further, as used in this specification and the appended claims, the singular forms "a", "an", and "the" include plural references unless the content clearly dictates otherwise. Thus, for example, "a volatile material" may include more than one volatile material The apparatus of the present invention delivers a volatile material in a substantially continuous manner when the apparatus is in a resting position (i.e. the apparatus is not being moved). The emission level of volatile materials may exhibit a uniform intensity until substantially all the volatile materials are exhausted. The continuous emission of the volatile materials can be of any suitable length, including but not limited to, up to: 20 days, 30 days, 60 days, 90 days, shorter or longer periods, or any period between 30 to 90 days.

The apparatus of the present invention is suitable for purposes of providing fragrances, air fresheners, deodorizers, odor eliminators, malodor counteractants, insecticides, insect repellants, medicinal substances, disinfectants, sanitizers, mood enhancers, and aromatherapy aids, or for any other purpose using a volatile material that acts to condition, modify, or otherwise change the atmosphere or the environment. For purposes of illustrating the present invention in detail, but without intending to limit the scope of the invention, the invention will be described in an air freshening system for delivering liquid containing perfume raw materials.

Referring to FIG. 1, an apparatus 10 in accordance with the present invention is shown. The apparatus 10 includes a delivery engine 100 and a housing 200.

Delivery Engine

Referring to FIG. 2, the delivery engine 100 comprises a width, length and depth along an x-axis, y-axis, and z-axis, respectively. The width, length, and depth may be such that the delivery engine 100 is considered compact and/or portable. By "compact" or "portable", it is meant that the delivery engine 100 can be conveniently and comfortably carried in a pocket, purse, or the like. The delivery engine 100 can be constructed as a disposable, single-use item or one that it is replenished with a volatile material.

The delivery engine 100 may include a lip 102 that defines the outer perimeter of the delivery engine 100 and may circumference a reservoir 110 for containing a volatile material as well as a collection basin 112. The delivery engine 100 may also include a rupturable substrate 120 secured to the reservoir 110; a rupture element 130 positioned adjacent to the rupturable substrate 120; and a breathable membrane 140 secured to the lip 102 and enclosing the rupturable substrate 120, reservoir 110, and collection basin 112.

The body 104 of the delivery engine 100 can be thermoformed, injection molded, or blow molded with any known material. In some embodiments, the body 104 includes all structural aspects of the delivery engine 100 minus the rupturable substrate 120, the rupture element 130, and breathable membrane 140. In other embodiments, the body 104 includes the rupture element 130. The body 104 may be made of a multi layer material which may include a barrier layer to prevent evaporation of a volatile component and at least one outer layer that allows a rupturable substrate 120 to be heat-sealed to the body 104. A suitable sealant layer would include a layer of polyethylene or polypropylene or any suitable polyolefin sealant that allows for a leak proof seal of the reservoir 110. Suitable materials to form the body 104 of the delivery engine 100 include plastics, such as Pentaplast Pentaform® 2101 available from Klockner. In some embodiments, the material is colored or non-colored see-through plastic. The see-through material permits observation of the liquid and end-of life.

Reservoir

The delivery engine 100 may comprise a reservoir 110 for holding a volatile material. The reservoir 110 includes a width, length, and depth along the x-axis, y-axis, and z-axis, respectively. The reservoir 110 may be elongate in that its width to length ratio is about 2:1 to about 4:1, alternatively about 1.5:1 to about 2.5:1. The reservoir 110 may have a width of about 45 mm to about 55 mm, alternatively about 51 mm; a length of about 15 mm to about 30 mm to about, alternatively about 23 mm; a depth of about 5 mm to about 15 mm, alternatively about 11 mm. The dimensions of the reservoir 110 may be such that it holds about 2 ml to about 50 ml of liquid containing a volatile material. Alternatively, the reservoir 110 may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of liquid containing a volatile material.

The reservoir 110 may include a bottom 114 and a single opening 116. The reservoir 110 may also have a ridge 122 circumferencing the single opening 116 or the upper edge of the reservoir 110. This ridge 122 may provide a generally flat surface upon which a rupturable substrate 120 may be secured. The ridge 122 allows the secured area of the rupturable substrate 120 to be located away from the inner walls of the reservoir 110 where the volatile material would be held.

It is contemplated that the delivery engine 100 of the present invention may comprise two or more reservoirs (not shown) which can be filled with the same or different volatile materials. The reservoirs may have any configuration that contacts the breathable membrane 140 upon rupture. For example, the reservoirs may be opposedly connected for use in a flippable device. In such a device, the breathable membrane 140 is fluidly connected between the reservoirs.

Rupturable Substrate

Still referring to FIG. 2, the delivery engine 100 includes a rupturable substrate 120. The rupturable substrate 120 may be configured in any manner that prevents the volatile material in the reservoir 110 from contacting the breathable membrane 140 prior to activating or rupturing the delivery engine 100. In one embodiment, the rupturable substrate 120 may enclose the reservoir, prior to activation, by extending across the single opening 116 securing to the ridge 122 of the reservoir 110. The rupturable substrate 120 may be secured by a layer of adhesives, heat and/or pressure sealing, ultrasonic bonding, crimping, and the like or a combination thereof.

The rupturable substrate 120 can be made of any material that ruptures with applied force, with or without the presence of an element to aid in such rupture. Because the rupturable substrate 120 is intended to contain a volatile material while in storage, it may be made from a layer of barrier material that prevents evaporation of the volatile material prior to its intended use and a layer of heat-sealable layer. Such materials may be impermeable to vapors and liquids. Suitable barrier materials for the rupturable substrate 120 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 120. Such coated barrier films include metalized PET, metalized polypropylene, silica or alumina coated film may be used. Any barrier material, whether coated or uncoated, may be used alone and or in combination with other barrier materials.

Rupture Element

The rupturable substrate 120 may be breached to release a volatile material by actuating a rupture element 130. The rupture element 130 can be injection, compression, or pressure molded using a polyolefin, such as polyethylene or polypropylene; polyester; or other plastics as known to be suitable for molding. The rupture element 130 could also be made by thermoforming with a discrete cutting step to remove parts not wanted.

The rupture element 130 may be positioned in a space 132 formed in the delivery engine body 104 that is adjacent to the rupturable substrate 120 and subjacent a breathable membrane 140. The space 132 may be configured such that the rupture element 132 is nested within the space 132 and enclosed by a breathable membrane 140, thus requiring no other means to hold the rupture element 132 in the delivery engine 100. In one embodiment, the rupture element 130 is positioned between and in contact with said rupturable substrate 120 and said breathable membrane 140. A rupture element 130 that is directly adjacent to the breathable membrane 140 may facilitate wetting of the breathable membrane 140. More specifically, liquid may wick between rupture element 130 and the breathable membrane 140 allowing for maintenance of a larger wetted surface area of the breathable membrane 140.

The rupture element 130 may be configured in any manner such that a user can manually actuate the rupture element 130 and breach the rupturable substrate 120 with relative ease. In one embodiment, a user may actuate the rupture element 130 by manually compressing it. In other embodiments, the rupture element 130 may breach the rupturable substrate 120 through contact with an element provided in a delivery engine housing that engages and compresses the rupture element 130. Suitable compression forces to breach the rupturable substrate 120 with a rupture element 130 may be less than about 25N, alternatively, less than about 20N, alternatively less than about 15N, alternatively less than about 10N, alternatively less than about 5N, alternatively from about 1N to about 15N, alternatively, from about 1N, to about 10N, alternatively, from about 1N to about 5N.

The compression force can be measured using an electromechanical testing system, QTest Elite 10, available from MTS, along with a modified UL 283 finger probe made of polyamide. The UL 283 finger probe is described in Standard for Air Fresheners and Deodorizers, UL Standard 283, FIG. 10.1 (UL Mar. 31, 2004). As described in UL 283, FIG. 10.1, the radius of the finger tip is 3.5 mm; height of the finger tip is 5 mm; depth of the finger tip is 5.8 mm. However, unlike the finger probe described in the aforementioned text, the modified UL 283 finger probe does not include any articulating joints. Instead, it is in a fixed position that is perpendicular to the rupture element 130 when testing is conducted. The testing occurs at ambient temperatures (23±2° C.). The perimeter of a delivery engine 100 is rested on a support fixture, without directly contacting or directly securing the rupture element 130 to the support fixture. The crosshead speed of the electromechanical testing system is set at 30 mm/min. The modified UL 283 finger probe is moved towards the rupture element 130 to contact a region where displacement is desired for rupturing a rupturable substrate 120. Where a flange 134 such as the one described herein is utilized, the desired region of displacement is the mid-point of the flange 134. The mid-point is the point that is half way between the proximal end and distal end 136. For example, where a flange 134 is 2 cm from proximal end to distal end 136, the mid-point is located at 1 cm. The machine is run until the rupture element 130 is displaced by 6 mm. Zero displacement is defined as the point at which 0.1N of force (i.e. preload) is applied. The load at the first peak where the rupturable substrate 120 is broken is recorded as the force to rupture. Those of ordinary skill in the art will appreciate that compression forces will vary depending on the physical properties and placement of the breathable membrane 140, rupture element 130, and rupturable substrate 120 in a delivery engine 100.

Figure 2:
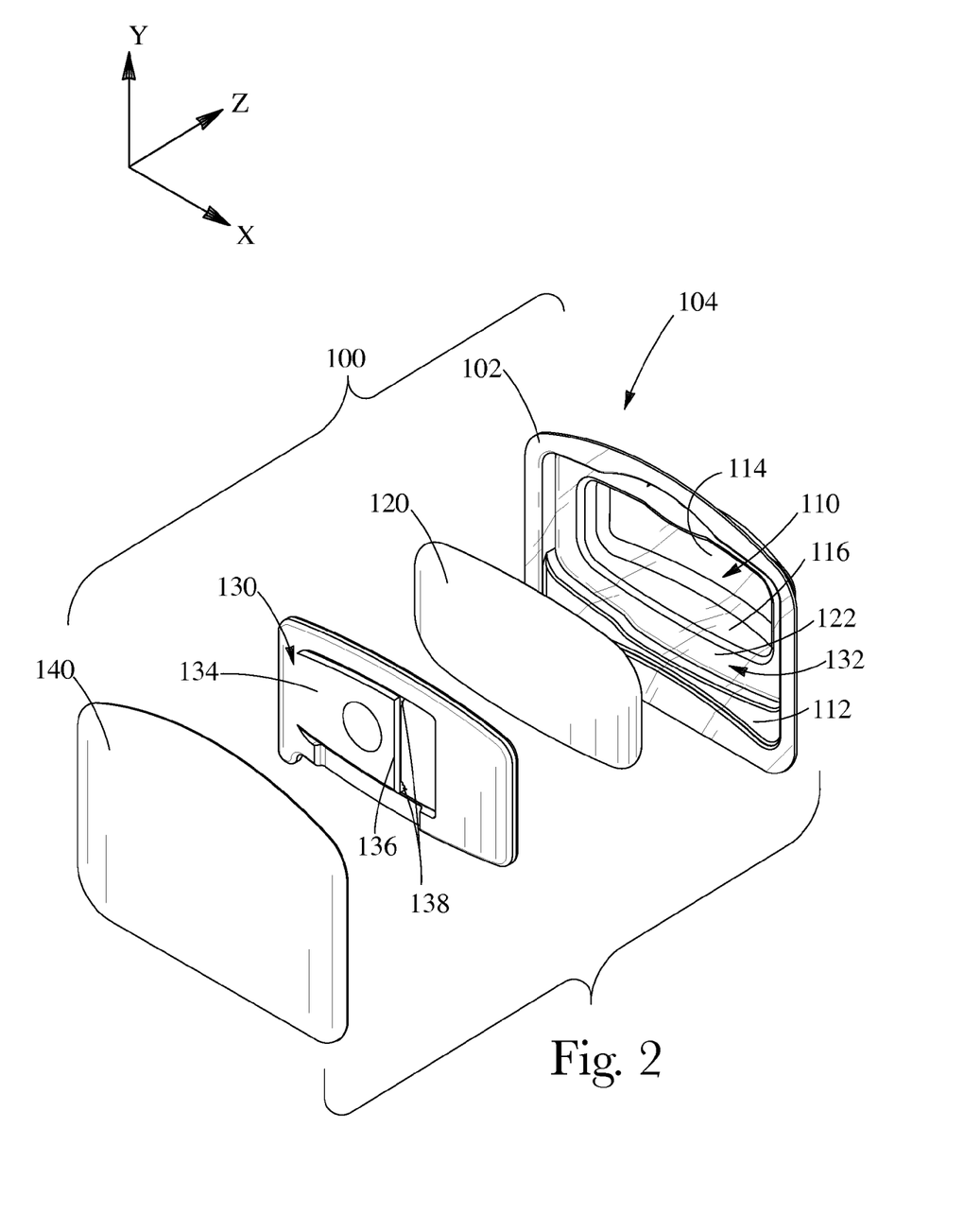

There are numerous embodiments of the rupture element 130 described herein, all of which are intended to be non-limiting examples. FIG. 2 shows one non-limiting embodiment of the rupture element 130. In this embodiment, the rupture element 130 includes a flange 134 hinged to the rupture element 130. The flange 134 may be injection molded and may include a distal end 136. The distal end 136 may include one or more piercing elements 138 located in the z-direction or towards the rupturable substrate 120. In one embodiment, the distal end 136 may include two spaced apart piercing elements 138 in the z-direction. In an alternate embodiment, the distal end 136 may form a single point (not shown) along the x-y plane. A user may manually compress or press downward in the z-direction on the flange 134 such that the rupturable substrate 120 is breached and a volatile material is released to the breathable membrane 140.

It is contemplated that the rupture element 130 may include more than one flange 134 where additional points of rupture are desired. For example, the rupture element 130 may include a first compressible flange and a second compressible flange opposedly hinged to said rupture element (not shown).

Figure 3:
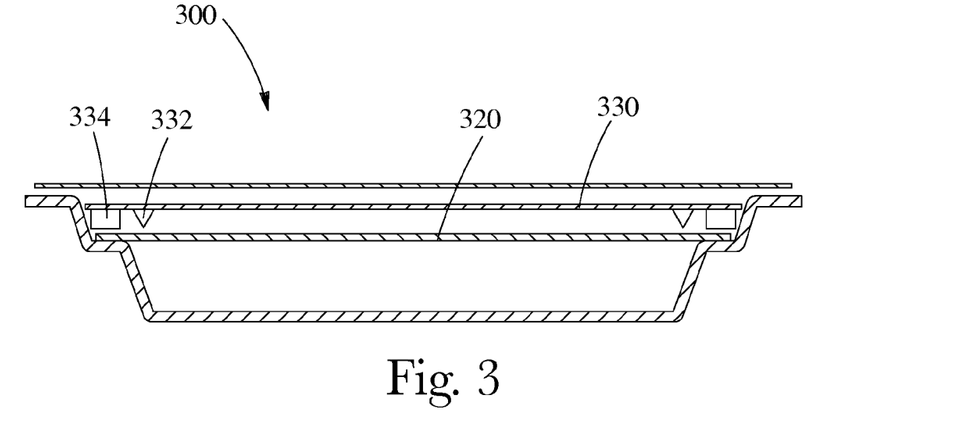

FIG. 3 shows another embodiment of a rupture element 330 which includes one or more piercing elements 332 supported on a corresponding spring-like part 334. The spring-like part 334 may be a metal coil, polyolefin or polyurethane foam, injection molded bristles, injection molded plastic spring or hinge parts, or the like. Upon pressing the rupture element 330 towards the rupturable substrate 320, one or more piercing elements 332 will puncture the rupturable substrate 320 and then return to its original position.

Figure 4:
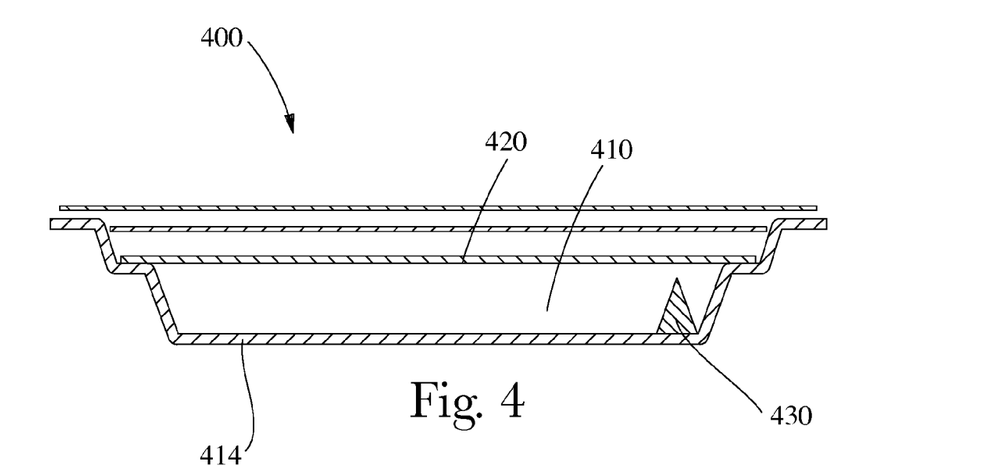

FIG. 4 shows another embodiment of a rupture element 430 where it is integrally formed with the reservoir 410. This can be accomplished by thermoforming, pressure forming, injection molding or any known means of forming plastic parts. The rupture element 430 in this embodiment, is a sharp piercing structure extending opposite from the interior bottom 414 of the reservoir. A user may compress the bottom 414 of the reservoir 410 to pierce the rupturable substrate 420 with the rupture element 430. This embodiment eliminates having to manufacture a separate rupture element 430, yet it performs the same function.

Collection Basin

Figure 5:
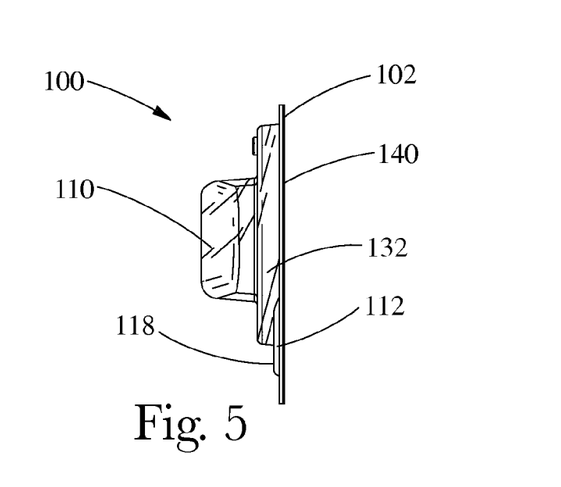
Figure 6:
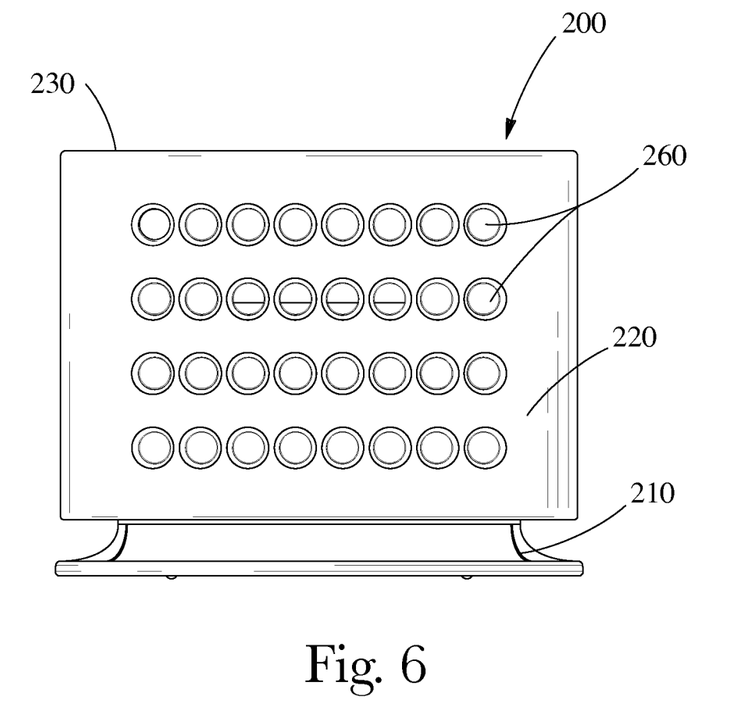
Figure 7:
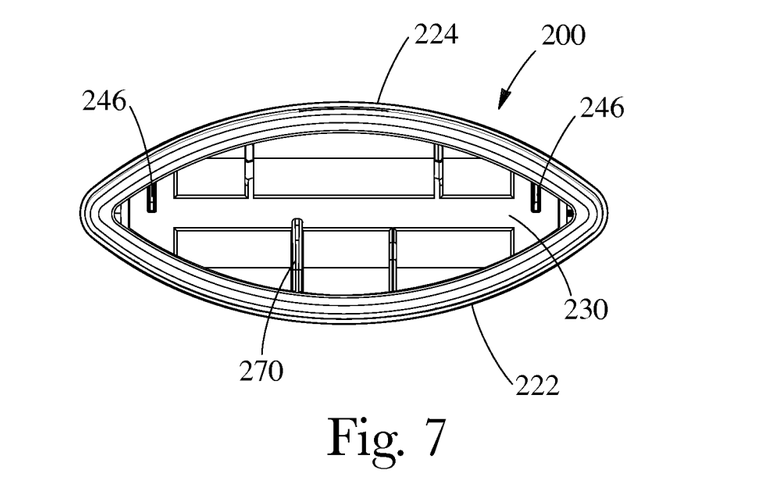

Now referring to FIG. 5, the delivery engine 100 may optionally include a collection basin 112 to collect volatile materials from the reservoir 110 after the rupturable substrate 120 is compromised. The collection basin 112 may be any size, shape or configuration, and may be made of any suitable material, so long as it is in fluid communication with the reservoir 110 and the breathable membrane 140 upon rupturing the rupturable substrate 120. It may be sized to collect any suitable volume of a volatile material to provide a controlled volume of the volatile material to the breathable membrane 140. In one embodiment, the collection basin 112 may be sized to collect about 1 ml to about 4 ml of volatile materials, alternatively about 1 ml to about 3 ml, alternatively about 1 ml to about 2.5 ml, alternatively about 1.5 ml to about 1.8 ml.

In one embodiment, the collection basin 112 may include a bottom 118 in the z-direction and a top that opens towards a breathable membrane 140. The breathable membrane 140 may lie across the open top, enclosing the collection basin 112 so liquid cannot flow freely out through the breathable membrane 140. The collection basin 112 may be integrally constructed with the body 104 of the delivery engine 100 in a thermoform part.

As shown in FIG. 5, in one embodiment, the collection basin 112 is positioned downwardly or opposite the y-direction from the reservoir 110. When the delivery engine 100 is placed upright, a volatile material naturally flows down the reservoir 110 into the collection basin 112 ensuring a controlled, continual dosing of the breathable membrane 140. Further, the collection basin 112 has depth along the z-axis which is smaller in depth than the reservoir 110. The bottom 118 of the collection basin lies closer to the breathable membrane 140 than the reservoir bottom 114, thus forming a step in the delivery engine 100. The proximity of the collection basin bottom 118 with the breathable membrane 140 helps to ensure a continual supply of volatile material and wet more surface area of the breathable membrane 140, even when very little volatile material remains in the delivery engine 100. When the liquid contact area of the breathable membrane 140 is greater, the evaporation rate of volatile materials is higher and fragrance intensity can be maintained over longer periods.

Membrane

The delivery engine 100 may include a breathable membrane 140. The breathable membrane 140 is vapor permeable and prevents free flow of liquid out of the membrane 140, thus addressing leakage problems.

The breathable membrane 140 may be secured to the lip 102 of the delivery engine 100 in the same manner as the rupturable substrate 120 is secured to the ridge 122 of the reservoir 110. The breathable membrane 140 encloses the reservoir 110, rupturable substrate 120, rupture element 130, and collection basin 112. In this way, the rupturable substrate 120 may be breached by compressing the breathable membrane 140 and the rupture element 130. Once breached, the volatile material flows out of the reservoir 110, contacts the breathable membrane 140, and is delivered to the atmosphere. Because the breathable membrane 140 is shielded from the volatile material until the rupturable substrate 120 is breached, the fragrance intensity may build slowly from zero to its equilibrium rate of release when the breathable membrane 140 is fully wetted.

While not wishing to be bound by theory, the physical characteristics of a membrane may affect the diffusion rate of volatile materials through the membrane. Such characteristics may include materials used, pore size, thickness, and evaporative surface area.

The breathable membrane 140 may be filled with any suitable filler and plasticizer known in the art. Fillers may include finely divided silica, clays, zeolites, carbonates, charcoals, and mixtures thereof. In one embodiment, the breathable membrane 140 may be filled with about 50% to about 80%, by total weight, of silica, alternatively about 60% to about 80%, alternatively about 70% to about 80%, alternatively about 70% to about 75%.

In one embodiment, the breathable membrane 140 may include a microporous membrane. The microporous membrane is vapor permeable and capable of wicking liquid, yet prevents free flow of liquid out of the membrane. The microporous membrane may have limited selectivity leaving behind fewer perfume materials. Membranes that are selective, such as traditional polyethylenes, may inhibit high molecular weight volatile materials and materials with low solubility in polyethylene from diffusing through. This may limit perfume formulations, for example in the field of air fresheners where it is typically desired to use formulations having a wide variety of volatile materials having different volatilities. For example, some membranes may preclude the diffusion of alcohols, such as linalool and dihydromyrcenol which are widely used in perfume applications. The microporous membrane may have an average pore size of about 0.01 to about 0.06 microns, alternatively from about 0.01 to about 0.05 microns, alternatively about 0.01 to about 0.04, alternatively about 0.01 to about 0.03, alternatively about 0.02 to about 0.04 micron, alternatively about 0.02 microns.

The breathable membrane 140 may have a thickness in the z-direction, of about 0.01 mm to about 1 mm, alternatively between about 0.1 mm to 0.4 mm, alternatively about 0.15 mm to about 0.35 mm, alternatively about 0.25 mm.

Those of ordinary skill in the art will appreciate that the surface area of the breathable membrane 140 can vary depending on the user preferred size of the delivery engine 100. In some embodiments, the evaporative surface area of the breathable membrane 140 may be about 2 $cm^2$ to about 100 $cm^2$, alternatively about 10 $cm^2$ to about 50 $cm^2$, alternatively about 10 $cm^2$ to about 45 $cm^2$, alternatively about 10 $cm^2$ to about 35 $cm^2$, alternatively about 15 $cm^2$ to about 40 $cm^2$, alternatively about 15 $cm^2$ to about 35 $cm^2$, alternatively about 20 $cm^2$ to about 35 $cm^2$, alternatively about 30 $cm^2$ to about 35 $cm^2$, alternatively about 35 $cm^2$.

Suitable breathable membranes 140 for the present invention include a microporous, ultra-high molecular weight polyethylene (UHMWPE) optionally filled with silica as described in U.S. Pat. No. 7,498,369. Such UHMWPE membranes include Daramic™ V5, available from Daramic, Solupor®, available from DSM (Netherlands), and Teslin™, available from PPG Industries, and combinations thereof. It is believed that these membranes allow a volatile material to freely dissipate, while containing liquid within the delivery engine 100.

Other suitable breathable membranes 140 include any permeable polymeric, thermoplastic, or thermoset material, including acetal, acrylic, cellulosic, fluoroplastic, polyamide, polyester, polyvinyl, polyolefin, styrenic, etc., alone, co-extruded, woven or non-woven, mixed or in combination with elastomers, rubber, solids, silicas, or combinations thereof. Also suitable are Hytrel™ available from Dupont or Lotryl™ available from Arkema.

In one aspect of the invention, the breathable membrane 140 may include a dye that is sensitive to the amount of volatile material it is in contact with to indicate end-of-life. Alternatively, the breathable membrane 140 may change to transparent when in contact with a fragrance or volatile material to indicate diffusion is occurring. Other means for indicating end-of-life that are known in the art are contemplated for the present invention.

Housing

Figure 1:
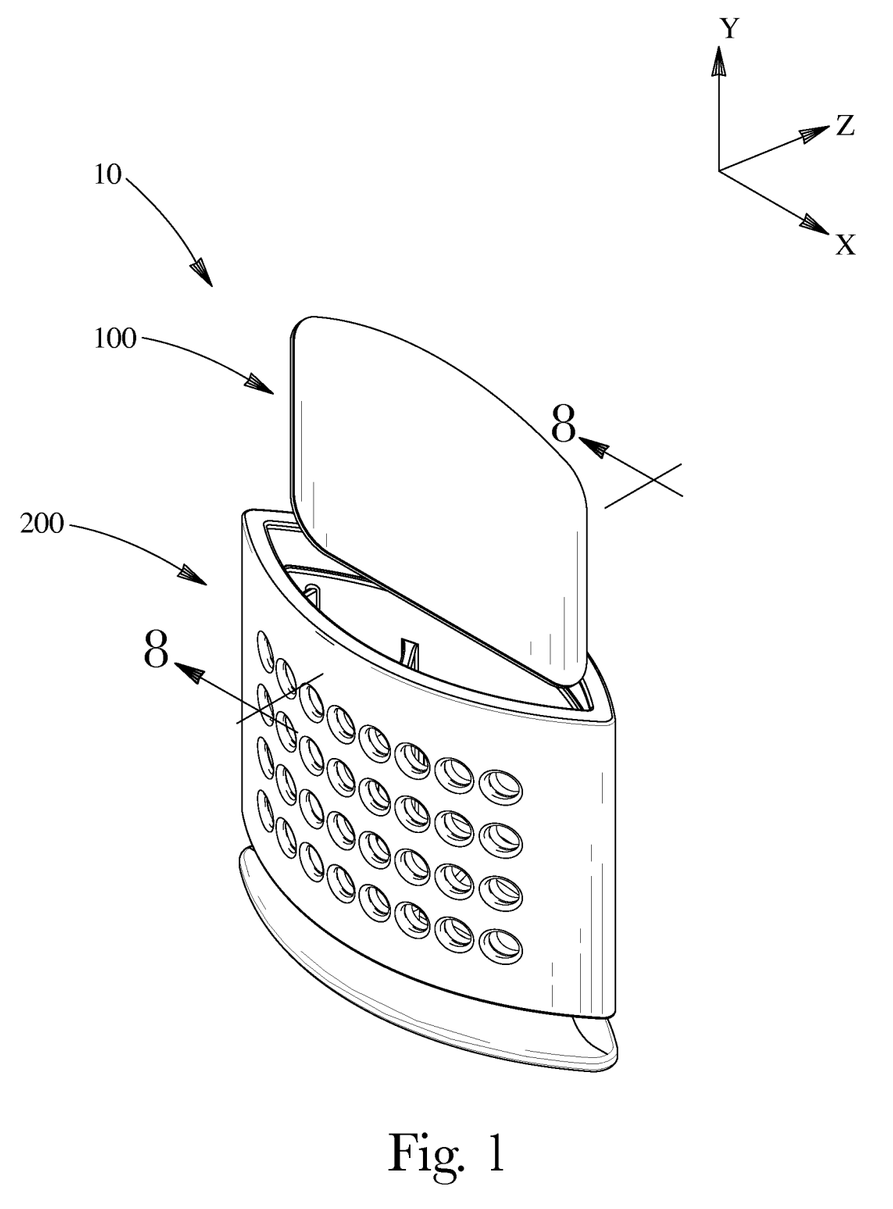

Now referring to FIGS. 6 to 9, the apparatus 10 of the present invention may include a housing 200 for releasably engaging the delivery engine 100. The housing 200 may comprise a width, length and depth along an x-axis, y-axis, and z-axis, respectively (as shown in FIG. 1). The housing 200 can be made of any suitable material such as glass, ceramic, wood, plastic, composite material, etc., and can have any size, shape and configuration suitable for encasing the delivery engine 100. The housing 200 can be rigid or flexible and can be made of material which allows the transfer of volatile materials to the surrounding environment. The housing 200 may include a base 210, a hollowed core 240 supported on the base 210 and nested internally within a shell 220. The housing 200 may also include a notch 270 and vents 260.

Shell and Hollowed Core

Figures 8, 9:
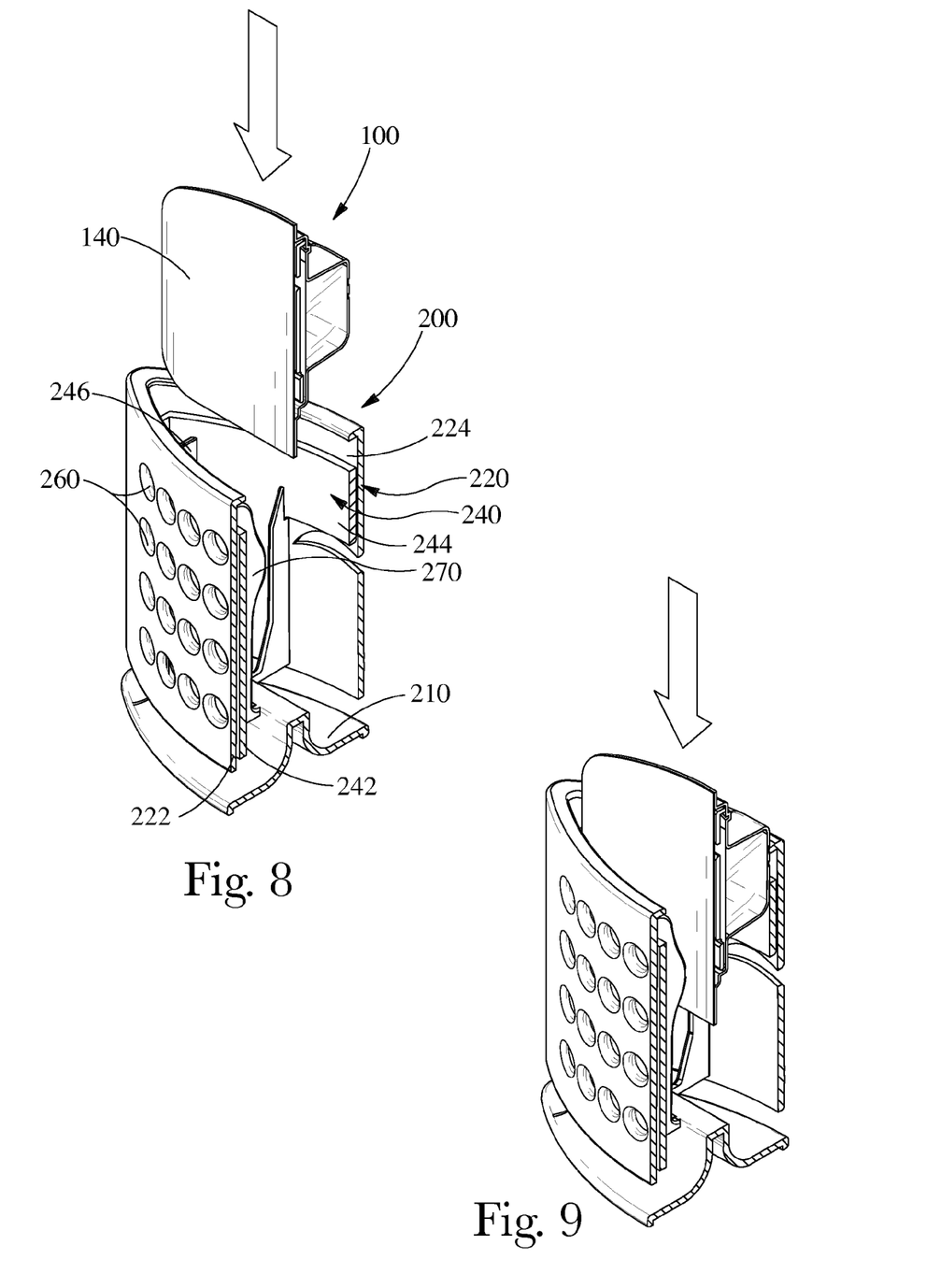

As seen in FIGS. 8 and 9, the housing 100 may include a hollowed core 240 supported on a base 210 and nested internally within a shell 220. The shell 220 may have a front wall 222 and a rear wall 224, both of which may be generally coextensive with a front wall 242 and a rear wall 244 of the hollowed core 240. The hollowed core 240 and shell 220 may be elliptically cylindrical and include a receiving end 230 for receiving the delivery engine 100. The receiving end 230 may be disposed remotely from the base 210 of the housing 200.

Ribs and Notches

The inner face of the rear wall 244 of the hollowed core 240 may include one or more retaining ribs 246 for guiding the delivery engine 100 downward into its final in-use position as seen in FIG. 9. In one embodiment, the retaining ribs 246 may include a first retaining rib and a second retaining rib positioned on the inner face of the rear wall 244 and which both extend longitudinally along the y-axis. The first and second retaining ribs may be positioned at the intersection of the front 242 and rear walls 244 of the hollowed core 240 to receive the lip 102 of the delivery engine 100.

The housing 200 may also include a notch 270, or a plurality of notches, to engage or compress the rupture element 130 as the delivery engine 100 is being received in the housing 200. In this way, a user is not required to manually activate the delivery engine 100 prior to its insertion into the housing 200. The notch 270 may be configured in any manner such that the delivery engine 100 can be inserted into the housing 200 with relative ease while the notch 270 compresses the rupture element 130 and breaches the rupturable substrate 120.

Suitable insertion forces to insert the delivery engine 100 which compresses the rupture element 130 and breaches the rupturable substrate 120 include less than about 25N, alternatively less than about 20N, alternatively less than about 15N, alternatively less than about 5N, alternatively from about 1N to about 25N, alternatively from about 1N to about 15N, alternatively from about 5N to about 20N, alternatively from about 5N to about 15N, alternatively about 8 to 15 N.

The insertion force can be measured using an electromechanical testing system, QTest Elite 10 available from MTS. The delivery engine 100 is clamped to the testing system and placed in the receiving end of the housing without any force against any notch 270 or elements that breach or help breach the rupturable substrate 120. The crosshead speed of the electromechanical testing system is set at 50 mm/min. The room temperature is 23±2° C. The machine is run until the rupturable substrate 120 is breached. Zero displacement is defined as the point at which 0.1N of force (i.e. preload) is applied. The load at the first peak where the rupture substrate 120 is broken is recorded as the force to rupture. Those of ordinary skill in the art will appreciate that insertion forces will vary depending on the physical properties and placement of the notch 270, breathable membrane 140, rupture element 130, and rupturable substrate 120.

In one embodiment, the notch 270 may be laterally off-set from the center of the front wall 242 of the hollowed core 240, so that less projection of the notch 270 in the z-direction is required when manufacturing. Thus, the breathable membrane 140 does not need to be stretched as far, resulting in less likelihood of damage.

The notch 270 and ribs 246 are configured such that the delivery engine 100 does not need to bend when inserting, resulting in lower insertion force. As the delivery engine 100 is inserted into the housing 200, the notch 270 compresses the breathable membrane 140 and the rupture element 130 in the direction of the reservoir 110 to breach the rupturable substrate 120 and release volatile materials to the breathable membrane 140. During insertion of the delivery engine 100, the ribs 246 guide the delivery engine 100 into contact and against the notch 270, maintaining the lateral position of the delivery engine 100 so the notch 270 fully engages the rupture element 130.

Vents

The housing 200 may have a plurality of vents 260 or apertures which align in a first, open position to facilitate delivery of the volatile material from the breathable membrane 140 to the atmosphere of the room or rooms that require treatment. Increasing the effective size of the vents 260, may increase the delivery of volatile material. Conversely, decreasing the effective size of the vents 260, may decrease the delivery of volatile material.

The vents 260 may be disposed anywhere on the housing 200. In the embodiment shown in FIGS. 6 to 9, the vents 260 are disposed on the front walls 222, 242 of shell 220 and hollowed core 240. The number and/or size of the vents 260 are not fixed. The size of the vents 260 can be controlled by the user through a variety of means. A user may open, partially open, partially close, or close the one or more vents 260 by sliding the shell 220 downwardly along the y-axis towards the base 210 such that the desired amount of emission is delivered to the location needing treatment. The housing 200 may also be constructed to enable open and closing of the vents 260 by rotation of the shell 240 around the x-axis (not shown). In addition to the vents 260, the housing 200 may have other means for visual inspection of the delivery engine 100.

The housing 200 may also include a clicking mechanism (not shown) to signal to the user that the housing 200 is in the desired open or closed position. Such clicking mechanism may include a first mating part (not shown) disposed along the outer face of the hollowed core 240 and a second mating part (not shown) disposed along the inner face of the shell 220.

The mating parts may frictionally engage the walls of the shell 220 and hollowed core 240 as they slide against one another. When the desired open or closed position is reached the mating parts may releasably lock into place and may provide a clicking sound.

Volatile Material

The apparatus 10 and/or the delivery engine 100 of the present invention deliver a volatile material to the atmosphere in a continuous manner. The term "volatile material" as used herein, refers to a material that is vaporizable at room temperature and atmospheric pressure without the need of an energy source. The volatile material may be a composition comprised entirely of a single volatile material. The volatile material may also be a composition comprised entirely of a volatile material mixture (i.e. the mixture has more than one volatile component). Further, it is not necessary for all of the component materials of the composition to be volatile. Any suitable volatile material in any amount or form, including a liquid or emulsion, may be used.

Liquid suitable for use herein may, thus, also have non-volatile components, such as carrier materials (e.g., water, solvents, etc). It should also be understood that when the liquid is described herein as being "delivered", "emitted", or "released," this refers to the volatilization of the volatile component thereof, and does not require that the non-volatile components thereof be emitted.

The volatile material can be in the form of perfume oil. Most conventional fragrance materials are volatile essential oils. The volatile material can be a volatile organic compound commonly available from perfumery suppliers. Furthermore, the volatile material can be synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. In the case of air freshener or fragrances, the different volatile materials can be similar, related, complementary, or contrasting.

The volatile material may also originate in the form of a crystalline solid, which has the ability to sublime into the vapor phase at ambient temperatures or be used to fragrance a liquid. Any suitable crystalline solid in any suitable amount or form may be used. For example, suitable crystalline solids include but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like.

It may not be desirable, however, for volatile materials to be closely similar if different volatile materials are being used in an attempt to avoid the problem of emission habituation. Otherwise, the people experiencing the emissions may not notice that a different material is being emitted. The different emissions can be provided using a plurality of delivery systems each providing a different volatile material (such as, musk, floral, fruit emissions, etc). The different emissions can be related to each other by a common theme, or in some other manner. An example of emissions that are different, but complementary might be a cinnamon emission and an apple emission.

In addition to the volatile material of the present invention, the delivery engine 100 may include any known malodor composition to neutralize odors. Suitable malodor compositions include cyclodextrin, reactive aldehydes and ionones.

While not wishing to be bound by theory, the continuous delivery of a volatile material may be a function of various factors including membrane pore size; membrane surface area; the physical properties of a volatile material, such as molecular weight and saturation vapor pressure ("VP"); and the viscosity and/or surface tension of the composition containing the volatile material.

The composition may be formulated such that the composition comprises a volatile material mixture comprising about 10% to about 100%, by total weight, of volatile materials that each having a VP at 25° C. of less than about 0.01 torr; alternatively about 40% to about 100%, by total weight, of volatile materials each having a VP at 25° C. of less than about 0.1 torr; alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. In one embodiment, the volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C. of about 0.1 torr to about 0.325 torr; and about 65% to about 100%, by total weight, of volatile materials each having a VP at 25° C. of about 0.035 torr to about 0.1 torr. One source for obtaining the saturation vapor pressure of a volatile material is EPI Suite™, version 4.0, available from U.S. Environmental Protection Agency.

Two exemplary compositions comprising a volatile material mixture having volatile materials of varying VPs are set forth below in Tables 1 and 2. These compositions are shown by way of illustration and are not intended to be in any way limiting of the invention.

TABLE 1

| Wt % | Low VP (torr) | High VP (torr) |
|---|---|---|
| 27.71 | 0.175 | 0.325 |
| 20.78 | 0.0875 | 0.1125 |
| 13.86 | 0.0625 | 0.0875 |
| 8.66 | 0.0375 | 0.0625 |
| 8.66 | 0.0175 | 0.0325 |
| 6.93 | 0.00875 | 0.01125 |
| 6.93 | 0.00625 | 0.00875 |
| 3.18 | 0.00375 | 0.00625 |
| 1.27 | 0.00175 | 0.00325 |
| 0.95 | 0.000875 | 0.001125 |
| 0.64 | 0.000625 | 0.000875 |
| 0.32 | 0.000375 | 0.000625 |
| 0.09 | 0.000175 | 0.000325 |

TABLE 2

| Wt % | Low VP (torr) | High VP (torr) |
|---|---|---|
| 33.38 | 0.175 | 0.325 |
| 25.75 | 0.0875 | 0.1126 |
| 19.07 | 0.0625 | 0.0875 |
| 13.86 | 0.0375 | 0.0625 |
| 4.00 | 0.0175 | 0.0325 |
| 1.50 | 0.00875 | 0.01125 |
| 0.50 | 0.00625 | 0.00875 |
| 0.72 | 0.00375 | 0.00625 |
| 0.55 | 0.00175 | 0.00325 |
| 0.27 | 0.000875 | 0.001125 |
| 0.20 | 0.000625 | 0.000875 |
| 0.13 | 0.000375 | 0.000625 |
| 0.07 | 0.000175 | 0.000325 |

The viscosity of a volatile material may control how and when a volatile material is delivered to the breathable membrane 140. For example, less viscous compositions may flow faster than the more viscous volatile materials. Thus, the membrane may be first wetted with the less viscous materials. The more viscous volatile material, being slightly less or of similar density with the less viscous phase, may remain in the collection basin 112 via gravity. Thus, the less viscous volatile material may be delivered to the breathable membrane 140 and emitted to the atmosphere more quickly. To help prevent liquid from seeping through the breathable membrane 140, volatile materials may have viscosities less than about 23 cP and surface tension less than about 33 mN/m.

In one embodiment, the composition containing a volatile material may have a viscosity of about 1.0 cP to less than about 25 cP, alternatively about 1.0 cP to less than about 23, alternatively about 1.0 cP to less than about 15 cP.

The composition containing a volatile material may be designed such that the composition may include a surface tension of about 19 mN/m to less than about 33 mN/m, alternatively about 19 mN/m to less than about 30 mN/m, alternatively about 19 mN/m to less than about 27 mN/m.

EXAMPLES

The following examples are not to be construed as limitations of the present invention since many variations thereof are possible without departing from its spirit and scope.

Example 1

In this example, two identical air freshening delivery engines are designed utilizing a Daramic V5 membrane with an evaporative surface area of approximately 34 cm². Two perfume compositions, RJJ-577 and RJJ-573-8, each having a volatile material mixture with volatile materials of different VP ranges are tested in the air freshening delivery engines for evaporation rates. The VP ranges of the volatile materials are shown in Tables 3 and 4.

TABLE 3

| RJJ-577 | | |
|---|---|---|
| VP 25° C. Low | VP 25° C. High | Wt % |
| 0 | 0.001 | 0.2 |
| 0.001 | 0.01 | 0.0 |
| 0.01 | 0.1 | 3.4 |
| 0.1 | 0.3 | 28.6 |
| 0.3 | 10 | 64.8 |

TABLE 4

| RJJ-573-8 | | |
|---|---|---|
| VP 25° C. Low | VP 25° C. High | Wt % |
| 0 | 0.001 | 1.9 |
| 0.001 | 0.01 | 8.5 |
| 0.01 | 0.1 | 32.6 |
| 0.1 | 0.3 | 49.8 |
| 0.3 | 10 | 6.8 |

Figure 10:
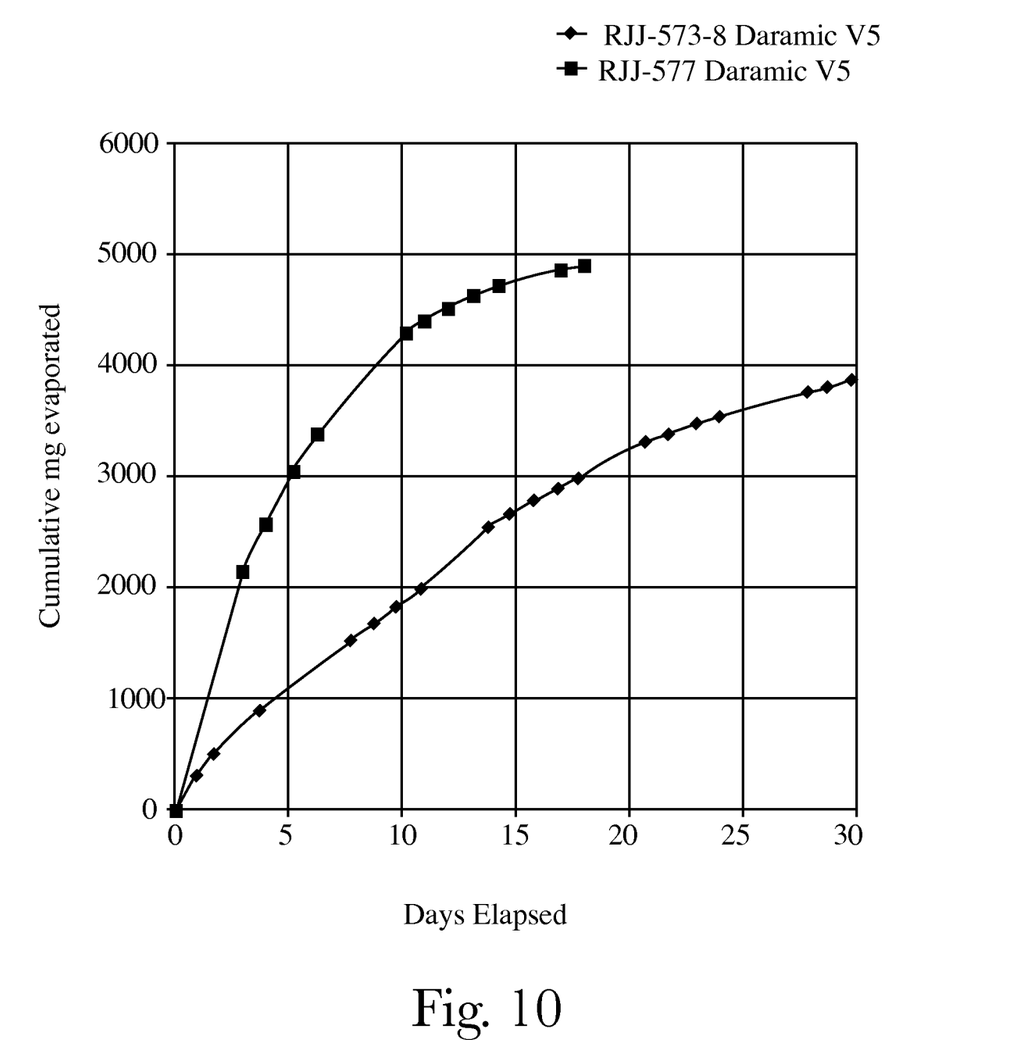

One delivery engine is loaded with 6000 mg of perfume composition RJJ-577; the other with 6000 mg of perfume composition RJJ-573-8. RJJ-577 includes relatively higher VP components than RJJ-573-8. Each filled delivery engine is weighed; weight is recorded. Both delivery engines are placed into housings and held in a room at 21° C. At the times indicated on FIG. 10, the delivery engine is weighed; weight recorded. FIG. 10 shows that after about two weeks, the evaporation rate of RJJ-577 has almost flattened which would then require another delivery engine. This would be costly and may be viewed as burdensome by consumers. On the other hand, perfume RJJ-573-8 with a microporous membrane delivers consistent linear intensity over a longer period of time.

Example 2

Figure 11:
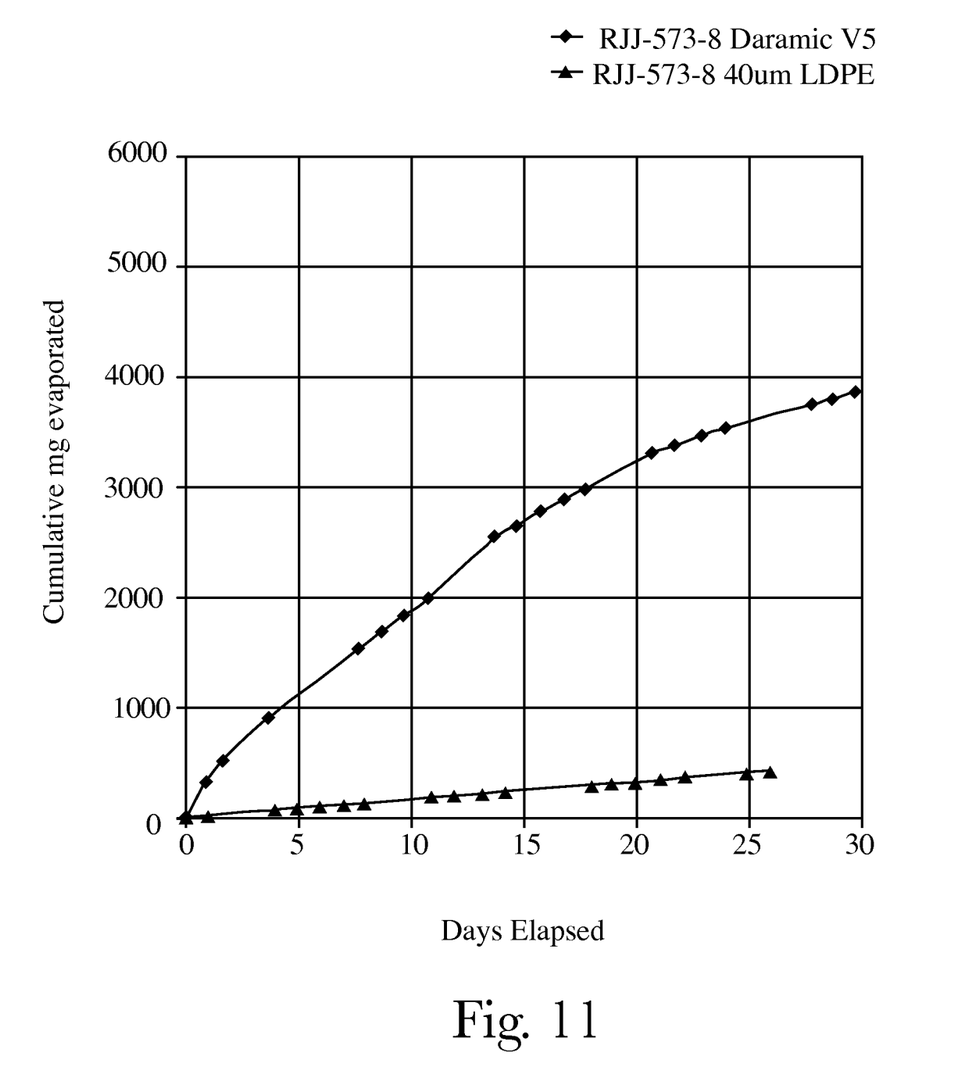

In this example, two air freshening delivery engines are constructed utilizing different membranes. Each is tested for evaporation rates using RJJ-573-8, which was utilized in Example 1. 6000 mg of RJJ-573-8 is loaded into a delivery engine with a low density polyethylene membrane (LDPE) having an average pore size of about 40 microns. 6000 mg of RJJ-573-8 is loaded into a delivery engine having a Daramic V5 microporous membrane. As can be seen from FIG. 11, the microporous membrane is much more efficient in releasing the relatively low vapor pressure perfume than the LDPE membrane. Thus, utilizing a microporous membrane in accordance with the present invention delivers higher intensities of lower vapor pressure (i.e. more pleasing "base note" perfume raw materials can be delivered).

Every numerical range given throughout this specification will include every narrower numerical range that falls within such broader numerical range, as if such narrower numerical range were all expressly written herein. Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An apparatus for delivering a volatile material comprising a delivery engine comprising:
   a. a reservoir comprising a volatile material mixture, said mixture comprising a volatile material mixture;
   b. a microporous membrane comprising an average pore size of about 0.01 to about 0.06 microns;
   c. a rupturable substrate enclosing said reservoir; and d. a rupture element comprising a support structure, said support structure is positioned between said rupturable substrate and said microporous membrane;
wherein said microporous membrane encloses said reservoir, said rupturable substrate, and said rupture element,
wherein the rupturable substrate is breached by compressing the microporous membrane and the rupture element.

2. The apparatus of claim 1, wherein said delivery engine further comprises a collection basin in fluid communication with said microporous membrane and said reservoir upon rupturing said rupturable substrate.

3. The apparatus of claim 1, wherein said rupture element comprises a compressible flange.

4. The apparatus of claim 3, wherein said compressible flange comprises a distal end and a piercing element, said piercing element positioned on said distal end.

5. The apparatus of claim 1, wherein said rupture element comprises a compression force to breach said rupturable substrate of less than about 15N.

6. The apparatus of claim 1, wherein said microporous membrane comprises an average pore size of about 0.02 microns.

7. The apparatus of claim 1, wherein said microporous membrane comprises an evaporative surface area of about 15 $cm^2$ to about 35 $cm^2$.

8. The apparatus of claim 1, further comprising a housing for receiving said delivery engine.

9. The apparatus of claim 1, wherein said microporous membrane comprising an average pore size of about 0.01 to about 0.03 microns.

10. An apparatus for delivering a volatile material comprising a delivery engine comprising:
a. a liquid reservoir comprising a volatile material mixture, said mixture comprising about 90% to about 100%, by total weight of said mixture, of volatile materials each having a VP at 25° C. of less than about 0.3 torr;
b. a rupturable substrate secured to said reservoir;
c. a compressible flange positioned adjacent to said rupturable substrate for rupturing said rupturable substrate;
d. a collection basin in fluid communication with said liquid reservoir upon rupturing said rupturable substrate; and
e. a microporous, ultra-high molecular weight polyethylene membrane enclosing said liquid reservoir, said rupturable substrate, said compressible flange, and said collection basin, wherein said membrane comprises a silica filler, an average pore size of about 0.01 microns to about 0.06 microns, and a thickness of about 0.01 mm to about 1 mm.

11. The apparatus of claim 10, wherein said compressible flange comprises a distal end and a piercing element, said piercing element positioned on said distal end.

12. The apparatus of claim 10, wherein said membrane comprises an evaporative surface area of about 15 $cm^2$ to about 35 $cm^2$.

13. An apparatus for delivering a volatile material comprising a delivery engine comprising:
a. a reservoir comprising a volatile material mixture;
b. a rupturable substrate secured to said reservoir;
c. a rupture element;
d. a microporous membrane enclosing said reservoir, said rupturable substrate, and said rupture element;
wherein said rupturable substrate is position subjacent said rupture element and said rupture element is positioned subjacent said microporous membrane, and wherein, when said rupturable substrate is breached by actuating said rupture element, said volatile material mixture passes transversely through said rupturable substrate and said rupture element and contacts said microporous membrane for diffusion to the atmosphere,
wherein the rupturable substrate is breached by compressing the microporous membrane and the rupture element.

14. The apparatus of claim 13, wherein said rupture element comprises a piercing element, wherein when said rupturable substrate is breached by actuating said rupture element, said volatile material mixture passes transversely through said rupturable substrate and said piercing element and contacts said membrane for diffusion to the atmosphere.

* * * * *